(12) United States Patent
Mantinband et al.

(10) Patent No.: US 9,857,210 B2
(45) Date of Patent: Jan. 2, 2018

(54) METHOD AND APPARATUS FOR MEASURING THE FLOW RATE OF A LIQUID

(75) Inventors: Jack Yehoshua Mantinband, Efrata (IL); Michael Adler, Kfar Vradim (IL)

(73) Assignee: Renal Sense Ltd., Jerusalem (IL)

( * ) Notice: Subject to any disclaimer, the term of this patent is extended or adjusted under 35 U.S.C. 154(b) by 217 days.

(21) Appl. No.: 14/125,348

(22) PCT Filed: Jun. 21, 2012

(86) PCT No.: PCT/IL2012/000249
§ 371 (c)(1),
(2), (4) Date: Dec. 11, 2013

(87) PCT Pub. No.: WO2012/176194
PCT Pub. Date: Dec. 27, 2012

(65) Prior Publication Data
US 2014/0116128 A1    May 1, 2014

(30) Foreign Application Priority Data
Jun. 23, 2011 (IL) .......................... 213767

(51) Int. Cl.
*G01F 1/68* (2006.01)
*G01F 1/684* (2006.01)
(Continued)

(52) U.S. Cl.
CPC ............... *G01F 1/68* (2013.01); *A61B 5/208* (2013.01); *G01F 1/6847* (2013.01); *G01F 1/69* (2013.01); *G01F 1/6965* (2013.01); *G01F 1/6986* (2013.01)

(58) Field of Classification Search
CPC .......... G01F 1/68; G01F 1/684; G01F 1/6842; G01F 1/69; G01F 1/6965; G01F 1/6986; A61B 5/208
(Continued)

(56) References Cited

U.S. PATENT DOCUMENTS

| 4,061,031 A | 12/1977 | Grimsrud |
| 4,685,470 A | 8/1987 | Sekii et al. |

(Continued)

FOREIGN PATENT DOCUMENTS

| CN | 101498596 A | 8/2009 |
| JP | H07-151572 A | 6/1995 |

(Continued)

OTHER PUBLICATIONS

Authors: Norbert Lameire, Wim Van Biesen, Eric Hoste and Raymond Vanholder, Title: The prevention of acute kidney injury: an in-depth narrative review Part 1: volume resuscitation and avoidance of drug- and nephrotoxin-induced AKI, Date: 2008, Publisher: Oxford University Press, NDT Plus, pp. 392-402.*

(Continued)

*Primary Examiner* — Lisa Caputo
*Assistant Examiner* — Roger Hernandez-Prewitt
(74) *Attorney, Agent, or Firm* — Roach Brown McCarthy & Gruber, P.C.; Kevin D. McCarthy

(57) ABSTRACT

The invention is an apparatus and method for measuring the flow rate of a liquid through a conduit. The apparatus is based on a flow rate meter which is adapted to accurately measure the volumetric flow rate of a liquid using a simple, cost and energy effective, and accurate method using only one temperature sensor. The method is based on applying a pulse of thermal energy to the flowing liquid and measuring the temperature increase as a function of time and energy input. By comparing these measurements to a calibration (Continued)

table made by performing similar measurements for known flow rates, the rate of flow can be determined. One application, which will be described to illustrate the features of the method and apparatus of the invention, is measurement of the flow rate of urine excreted by a catheterized patient.

12 Claims, 10 Drawing Sheets

(51) Int. Cl.
  *G01F 1/69* (2006.01)
  *G01F 1/696* (2006.01)
  *G01F 1/698* (2006.01)
  *A61B 5/20* (2006.01)
(58) Field of Classification Search
  USPC .............................. 73/204.11, 204.14, 204.18
  See application file for complete search history.

(56) References Cited

U.S. PATENT DOCUMENTS

| | | | |
|---|---|---|---|
| 5,119,674 A | | 6/1992 | Nielsen |
| 6,604,417 B1 * | | 8/2003 | Koike et al. ............... 73/204.22 |
| 6,672,154 B1 * | | 1/2004 | Yamagishi et al. ........ 73/204.22 |
| 6,983,214 B2 | | 1/2006 | Hiraizumi et al. |
| 7,261,004 B2 * | | 8/2007 | Breen et al. .......... G01F 1/6986 73/861.95 |
| 2007/0237206 A1 * | | 10/2007 | Kubota et al. ................ 374/164 |
| 2009/0000396 A1 * | | 1/2009 | Kawanishi et al. ....... 73/861.95 |
| 2009/0314101 A1 * | | 12/2009 | Levine ....................... 73/861.08 |
| 2010/0028979 A1 * | | 2/2010 | Faulkner et al. .......... 435/284.1 |

FOREIGN PATENT DOCUMENTS

| | | |
|---|---|---|
| JP | 2009-288085 A | 12/2009 |
| JP | 2010-509018 A | 3/2010 |
| JP | 2010-117159 A | 5/2010 |
| JP | 2011-501188 A | 1/2011 |
| WO | WO 2004011886 A2 * | 2/2004 ............. G01F 1/696 |
| WO | 2004100788 A1 | 11/2004 |
| WO | 2009054940 A2 | 4/2009 |

OTHER PUBLICATIONS

George Shortley et al., Elements of Physics for Students of Science and Engineering, Third Edition—fourth printing, 1964, pp. 334-335, title page and verso of the title page.
Supplementary European Search Report for a counterpart foreign application which is identified as EP 12 80 2126—3 pages—dated Nov. 6, 2014.
International Search Report from a foreign patent office in a counterpart PCT application which is identified as PCT/IL2012/000249, 2 pages, dated Sep. 24, 2012.
Communication from a foreign patent office (Japanese patent office) in a counterpart foreign application—JP2014516494—dated Jun. 21, 2016; 3 pages for the office action in Japanese and 3 pages for the translated office action.

* cited by examiner

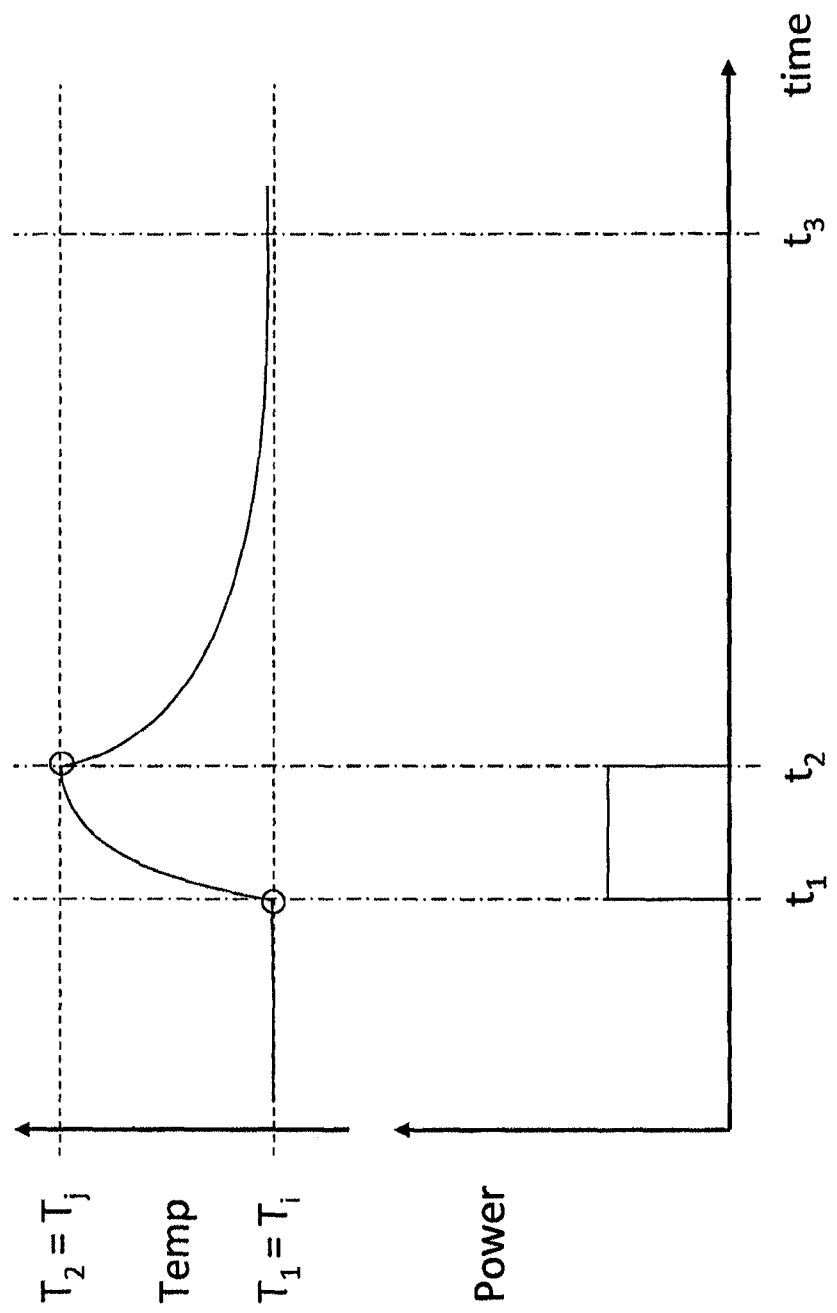

METHOD AND APPARATUS FOR MEASURING THE FLOW RATE OF A LIQUID

FIELD OF THE INVENTION

The present invention relates to the field of flow rate meters. Specifically, the invention relates to flow rate meters which enable the accurate determination of the volumetric flow rate of a liquid.

BACKGROUND OF THE INVENTION

Flow rate measurement is important in many fields. For example, many industrial processes require measurement of flow rate through various conduits in order to control the process appropriately. Other uses requiring measurement of a liquid or gas include delivery of a product to a consumer, such as gas, oil, and water.

In the medical field, liquid measurement is sometimes applied to a patient's urine output or to a medicine being administered intravenously. Acute kidney injury (AKI) is a common problem in hospitalized patients, particularly in critical care and in the operating room. However, only recently has the medical profession formulated criteria for assessing and classifying the risk and progression of AKI. These criteria specify five major stages in the progression of AKI: Risk, Injury, Failure, Loss, End stage renal disease, (known by their initials as the RIFLE criteria). Based on the success of RIFLE, the Acute Kidney Injury Network— AKIN—was formed by an international cadre of leading clinicians focused on the issue of AKI. AKIN has endorsed and promoted RIFLE. In addition, they also proposed minor modifications to the RIFLE criteria which they refer to as the AKIN criteria. The RIFLE-AKIN criteria provide valuable tools for preventing AKI. These criteria include measurements of creatinine clearance and urine output. Creatinine clearance is a very late indicator showing only that AKI has already occurred. Urine output as a measurement of kidney function is typically assessed on a daily or shift-wise (e.g., eight-hours) basis.

Thermal transfer flow rate meters typically measure flow rate continuously using a heating element and two temperature sensors (one upstream and one downstream from, or adjacent to, the heater). By measuring the temperature differential between the two thermometers, the flow rate is calculated. Alternatively, the temperature is kept at a constant value above the ambient temperature of the fluid at the heater and the energy required to do so is monitored, from which the flow rate can be calculated.

FIG. 1 schematically shows the basic arrangement of a prior art thermal mass flow rate meter. A liquid flows through a tube 100 in a direction indicated by the arrows. At some location in a wall of the tube or in the interior of the tube is placed a heating element 120. Temperature sensor 110, which measures temperature $T_i$, and temperature sensor 112, which measures temperature $T_j$, are located respectively upstream and downstream of heater 120. Isothermal lines 130, 131, and 132 symbolically show the temperature distribution as a result of the power input to the heating element, where the $T_{130} > T_{131} > T_{132}$.

The calculation for determining the flow rate is according to the equation:

$$Q = C_p \cdot m \cdot \Delta T \quad \text{equation 1}$$

substituting $m = \rho V$ $$Q = C_p \cdot \rho V \cdot \Delta T \quad \text{equation 2}$$

dividing both sides by t and solving for $\dot{V} = V/t$ $$\dot{V} = Q \div [t \cdot \rho \cdot C_p \cdot (T_j - T_i)] \quad \text{equation 3}$$

noting that $Q = I \cdot v \cdot t$ $$\dot{V} = I \cdot v \div [\rho \cdot C_p \cdot (T_j - T_i)] \quad \text{equation 4}$$

wherein the symbols used herein are defined in the following table:

| Symbol | Meaning | Units |
|---|---|---|
| V | Volume | [l] Liters |
| $\dot{V}$ | Volumetric Flow Rate (volume/time) | $\left[\frac{l}{\min}\right]$ Liters/minute |
| Q | Energy, work | [J] Joules |
| ρ | Density | $\left[\frac{g}{l}\right]$ grams/liter |
| $C_p$ | Specific Heat Capacity (under constant pressure) | $\left[\frac{J}{g \cdot {}^\circ C.}\right]$ Joules/(gram·°C.) |
| T | Temperature | [° C.] degrees Celsius |
| $T_i$ | Temperature of liquid before the heater (upstream) | [° C.] degrees Celsius |
| $T_j$ | Temperature of liquid after or at the heater (downstream) | [° C.] degrees Celsius |
| I | Electric Current | [A] Amperes |
| v | Electric potential | [v] Volts |
| ΔT | Temperature Difference $T_j - T_i$ | [° C.] degrees Celsius |
| t | Time | [s] seconds |

A related type of thermal transfer flow rate meter, known, inter alia, as a constant temperature flow rate meter, uses a similar arrangement to that shown in FIG. 1 with the exception that temperature sensor 112 is adjacent to, or integral with heating element 120. In this configuration, the heating element 120 is heated to a set constant differential temperature $T_j$ (as measured by sensor 112) above the temperature $T_i$ measured by sensor 110. The amount of heat carried away by the flowing fluid depends on the flow rate. The temperature of heater 120 is kept constant by adjusting the current applied thereto. The value of the electric current (I) required in order to maintain a constant temperature differential ΔT provides a means to calculate the flow rate, as shown in equation 4.

In the above basic arrangement of a prior art thermal mass flow rate meter a quantity of heat is applied to the fluid by heating element 120 until the temperature reaches a value $T_j$. At this point the heating element is turned off and the time is measured until the temperature returns to the original value $T_i$. The time of the first measuring point is accurately known but it is difficult to determine the exact time at which the second measurement should be taken, since the temperature changes relatively slowly as it approaches its steady state value. Furthermore, when making repeated measurements of the flow rate the ambient temperature of the liquid may slowly increase, thus an accurate value of $T_i$ of the liquid is not obtained. Moreover, the use of a prior art thermal mass flow rate meter, which requires that energy be continuously applied to the heating element, is not energy efficient.

It is therefore an object of the present invention to provide a simple and accurate method for determining the flow rate of a liquid.

It is another object of the invention to provide a simple, cost effective and accurate flow rate meter.

It is another object of the invention to provide a flow rate meter that has a minimal energy requirement.

Further purposes and advantages of this invention will appear as the description proceeds.

SUMMARY OF THE INVENTION

In a first aspect the invention is an apparatus for measuring the volumetric rate of flow of a liquid through a conduit. The apparatus comprises the following components:
 a) a heating element in thermal contact with the liquid in the conduit, the heating element adapted to deliver a known quantity of heat to the flowing liquid;
 b) a temperature sensor adapted to measure the instantaneous temperature of the heating element; and
 c) a control system that comprises at least one of the following components: a processor, input means, a memory unit, display devices, and output means, wherein the components of the control system are configured to:
  i) activate the heating element to deliver the known quantity of heat;
  ii) receive the measurements of the instantaneous temperature of the heating element from the temperature sensor;
  iii) retrieve from the memory unit pre-stored calibration data relating changes in the temperature of the heating element to known flow rates of the liquid; and
  iv) use the known quantity of heat, the measurements of the instantaneous temperature of the heating element, and the pre-stored calibration data to determine the volumetric flow rate.

In embodiments of the apparatus the components of the control system are configured to carry out at least one of the following:
 a) to store and display to a user information related to the operation of the apparatus and the properties of the liquid that are measured or determined by components of the apparatus;
 b) to send instantaneous or historical values of measured temperatures and other information relative to the liquid and the apparatus to remote locations;
 c) to send signals that can be used as input to other systems; and
 d) to send alarms if there are predetermined changes in the flow rate or other measured properties of the liquid.

Embodiments of the apparatus can comprise at least one of:
 a) a bubble trap located upstream of the measurement location;
 b) a gas-permeable membrane located upstream of the measurement location;

The apparatus can be adapted to be either connected to or an integral part of a conduit. In embodiment of the apparatus the conduit is a catheter or drainage tube leading from a patient. The control system of the apparatus can be configured to detect risk of acute kidney injury and stages thereof.

In a second aspect the invention is a method for real-time measuring the volumetric rate of flow of a liquid through a conduit. The measurement is made by use of an apparatus comprising a heating element in thermal contact with the flowing liquid and adapted to deliver a known quantity of heat to the flowing liquid, a temperature sensor adapted to measure the instantaneous temperature of the heating element, and a control system comprising a processor and a memory unit. The method comprises the following steps:
 i) measuring the temperature $T_i$ of the heating element;
 ii) activating the heating element to deliver a known quantity of heat to the flowing liquid;
 iii) measuring the temperature $T_j$ of the heating element immediately after the known quantity of heat has been delivered to the flowing liquid;
 iv) determining from the measurements the value of $\Delta T = T_j - T_i$;
 v) recalling from a memory a calibration table, graph, or mathematical relationship that was constructed for the known quantity of heat and determining from the table, graph, or mathematical relationship the value of the flow rate that corresponds to the measured value of $\Delta T$.

Embodiments of the method of the invention are adapted to measure the volumetric flow rate of a liquid through a catheter or a drainage tube leading from a patient. The flowing liquid may be urine. In embodiments of the method in which the flowing liquid is urine, the measurements can be used to detect risk of acute kidney injury and stages thereof.

In another aspect the invention is a method of using a heating element in thermal contact with liquid flowing through a conduit and adapted to deliver a known quantity of heat to the flowing liquid and a temperature sensor adapted to measure the instantaneous temperature of the heating element to construct a calibration table, graph, or mathematical relationship that can be used to determine the value of the flow rate that corresponds to a measured value of $\Delta T$ for a known quantity of heat delivered by the heating element. The method comprises the following steps:
 a) adjusting the flow rate to a known constant value;
 b) measuring the temperature $T_i$ of the heating element;
 c) activating the heating element to deliver the known quantity of heat to the flowing liquid;
 d) measuring the temperature $T_j$ of the heating element immediately after the known quantity of heat has been delivered to the flowing liquid;
 e) determining $\Delta T = T_j - T_i$;
 f) storing the values of the flow rate, the quantity of heat, and $\Delta T$ in a memory unit; and
 g) repeating steps a to f for different known values of flow rate.

BRIEF DESCRIPTION OF THE DRAWINGS

The above and other characteristics and advantages of the invention will be more readily apparent through the following examples, and with reference to the appended drawings, wherein:

FIG. 3A, FIG. 3B, and FIG. 3C schematically shows graphs of a single heating pulse applied to the apparatus and the corresponding temperature change vs. time;

DETAILED DESCRIPTION OF PREFERRED EMBODIMENTS

The present invention is a method and apparatus for measuring the flow rate of a liquid through a conduit. The apparatus is based on a flow rate meter which is adapted to accurately measure the volumetric flow rate of a liquid in a simple, cost and energy effective, and accurate method using only one temperature sensor. The method is based on applying a pulse of thermal energy to the flowing liquid and measuring the temperature increase as a function of time and energy input. By comparing these measurements to a calibration table made by performing similar measurements for known flow rates, the rate of flow can be determined. One application, which will be described to illustrate the features of the method and apparatus of the invention, is measurement of the flow rate of urine excreted by a catheterized patient.

Figure 1:
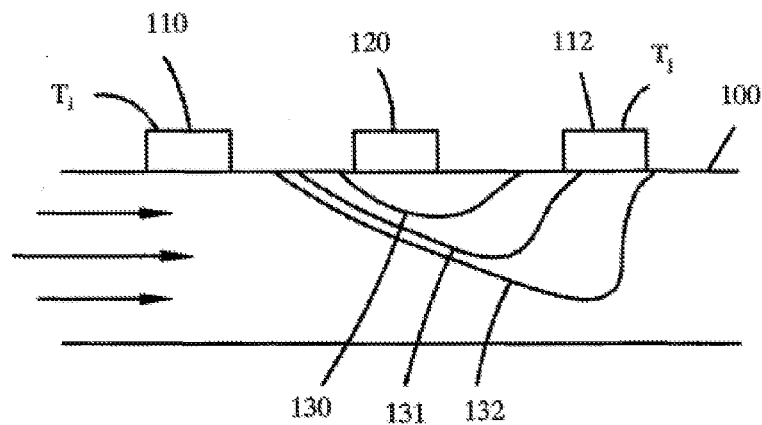
FIG. 1 schematically shows the basic arrangement of a prior art thermal transfer flow rate meter.
Figure 2:
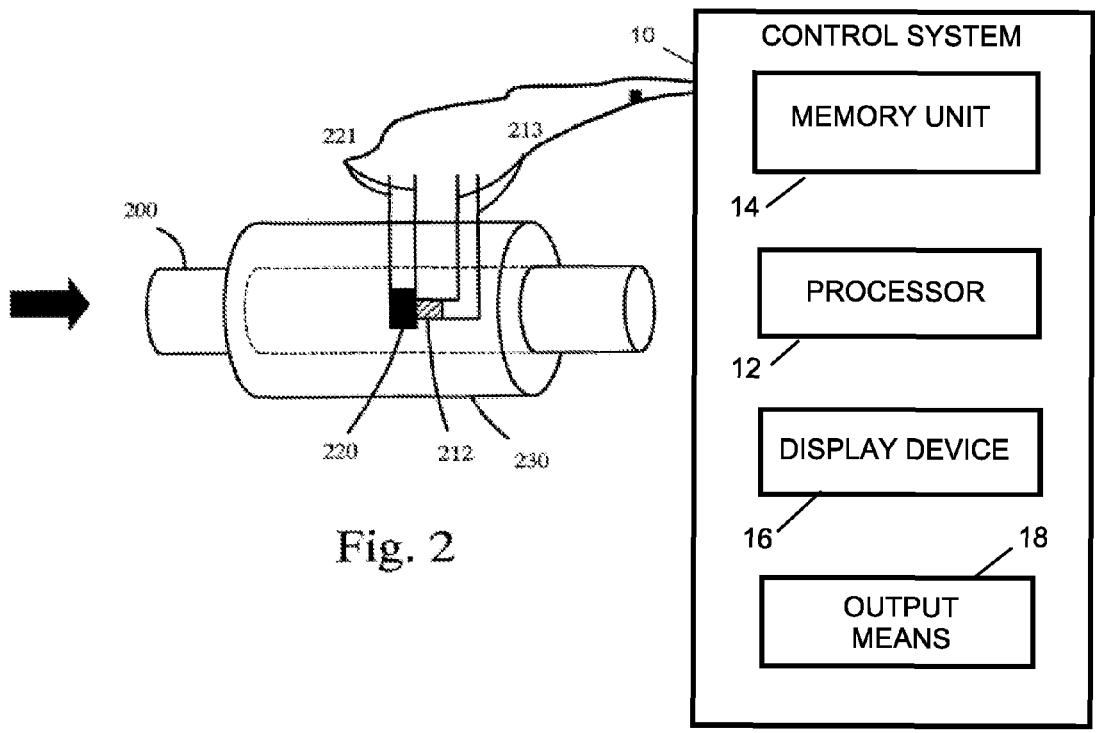
FIG. 2 schematically shows a section of conduit comprising components used for measuring the flow rate of a liquid flowing through it according to an embodiment of the invention.

FIG. 2 schematically shows a section of conduit 200 (e.g., tubing, catheter, or pipe) comprising components used for measuring the thermal mass flow rate of a liquid flowing through it in the direction indicated by the arrow. Heating element 220 is shown located inside conduit 200 inserted directly into the flowing liquid. In another embodiment element 220 is located on a heat-conductive portion of wall of the conduit. Electric power is supplied to heating element 220 by applying a voltage via the leads 221. Adjacent to, or integral with heating element 220 is a temperature sensor 212 that measures the temperature of the heating element 220. The temperature measured by sensor 212 is read out via the leads 213. To minimize heat loss the section of conduit that contains heating element 220 and temperature sensor 212 is preferably thermally isolated from the surroundings using optional insulation 230.

Many different sources of heat can be used for the heating element 220. Possible heating means 220 include for example, electric resistors and thermistors or appropriately adapted metered heat exchangers. The measurement of energy input and the way of applying it to the heating element 220 is accomplished by techniques that are well known in the art according to the source of heat used.

Thermal sensors that can be used in the flow rate meters of the present invention include, for example, transistors, thermocouples, thermistors, thermopiles and other types of thermal sensors that are currently known in the art or may be known in the future.

Although the heating element and temperature sensor are described herein as separate elements for convenience of describing their respective functions, embodiments are possible wherein a single element, e.g. a self-heating thermistor or resistive thermal device (RTD), can be used to enable both the heating and the temperature measurement functions.

In some applications it may be necessary to ensure that bubbles that would affect the accuracy of the measurements are eliminated from the liquid at the location where the measurements are being made. To accomplish this one or more bubble traps may preferably be employed upstream of the measurement locations. Alternatively, or in combination with the bubble trap, ventilation means to allow gases to escape from the conduit, such as a gas-permeable membrane may preferably be located upstream of the measurement location.

At some conduit orientations and flow rates the conduit or sub-conduit may not be filled at the measurement location. Therefore, for some applications a check valve should be installed downstream of the measurement spot in order to create a sufficient back pressure to insure complete filling of the conduit at the location of the measurements.

The leads, 213, 221 are connected to a control system 10 which comprises an electrical circuit or a processor 12 adapted to activate the heating element at predetermined times, to receive data from the temperature sensors and devices, e.g. ammeters to measure the input of energy to the heating element, and to use this data to determine the flow rate. The control system may also comprise input means, e.g. a keypad, a keyboard, buttons, switches, a touch screen, a touch pad, a trackball, a mouse or other pointing device or other input means to allow a user to control parameters such as the length of time and/or quantity of heat energy that should be applied and the frequency with which the measurements are made. The control system may also comprise one or more memory units 14, display units 16, and output means 18 to store and display to the user parameters of the system. The output means may comprise communication devices that can be adapted to send the instantaneous or historical data to remote locations by using wired or wireless technologies. In addition the control system may be adapted to use the output means to send signals that provide input to other systems. For example, in a hospital setting, the control system can be adapted to send an alarm to a nurse's station if the flow rate of urine from a catheterized patient to a collection bag falls below a predetermined rate, or to send an alarm if any irregularity occurs in the flow rate of a medicine being administered intravenously. In the case of urine measurement, the control system may be adapted to use the measurements to provide on-going, real-time assessment of kidney function and early warning of conditions related to AKI.

As in the prior art, the flow rate is determined by use of the equation:

$$Q = C_p \cdot \rho \cdot \dot{V} \cdot \Delta T \qquad \text{equation 2}$$

Solving for $\dot{V}$:

$$\dot{V} = Q \div [C_p \cdot \rho \cdot \tau \cdot (T_f - T_i)] \qquad \text{equation 3}$$

According to the method of the present invention it is assumed that, for a given liquid, ρ and $C_p$, which represent the liquid properties, are constants and can be defined as:

$$K = \frac{1}{\rho \cdot C_p} \qquad \text{Equation 5}$$

Thus, $$V = K \cdot Q \div [t \cdot (T_j - T_i)] = K \cdot Q \div [t \cdot \Delta T] \qquad \text{Equation 6}$$

Accordingly, for a given period of time, change in temperature ($\Delta T$) is a function of the flow rate (and vice versa) and for constant Q, as one increases the other decreases. For example, when the flow rate is greater, more heat is transferred away from the heating element and $\Delta T$, i.e. (the extent to which the heating element achieves a higher temperature relative to the non-heated (ambient) state is smaller. Conversely, when the flow rate is slower, less heat is transferred away from the heating element and $\Delta T$ is greater.

An embodiment of the method of the invention is illustrated with reference to FIG. 2 and FIG. 3A. The temperature of the heating element 220 is first measured by temperature sensor 212. This measurement is indicated as $T_i$ in the upper curve (Temperature vs. time) in FIG. 3A. Following the measurement of temperature $T_i$, a known or measured quantity, or dose, of energy is applied to the heating element 220 in a fashion appropriate to the source of heat. Finally, the temperature $T_j$ of the heating element is measured immediately upon completion of the measured dose of energy, at time designated $t_2$.

Doses of energy can be applied to the heating element 220 in variety of ways, for example electrical energy can be applied to a resistive heating element in one of the following ways:

a. by applying a set power level (e.g., watts) over a set period of time e.g., 1 W for 60 seconds or 50 mW for 10 seconds, depending on the heating element and temperature sensor used; or b. by discharging a capacitor circuit that has been charged from a given first voltage level to a given second voltage level; or c. by using a coil boost circuit comprising a transistor to deliver a measured series of current "micro-pulses" which combine to give a specific "macro-pulse".

FIG. 3A illustrates substantially one period of measurement. In this example the power curve (lower curve showing input power vs. time) illustrates that a square heating power pulse is applied beginning at time $t_1$ corresponding to temperature $T_1$ and ending at time $t_2$ corresponding to temperature $T_2$. This results in the temperature development detection curve shown at the top. In this case, the change in temperature is measured over the entire duration of the pulse, i.e. $\Delta T = T_2 - T_1 = T_j - T_i$.

The temperature measurements to determine $\Delta T$ do not necessarily have to be linked to the duration of the heating pulse. For example referring to FIG. 3B, $T_i$ is measured at a time after $t_1$ and $T_j$ is measured before $t_2$.

Figure 3B:
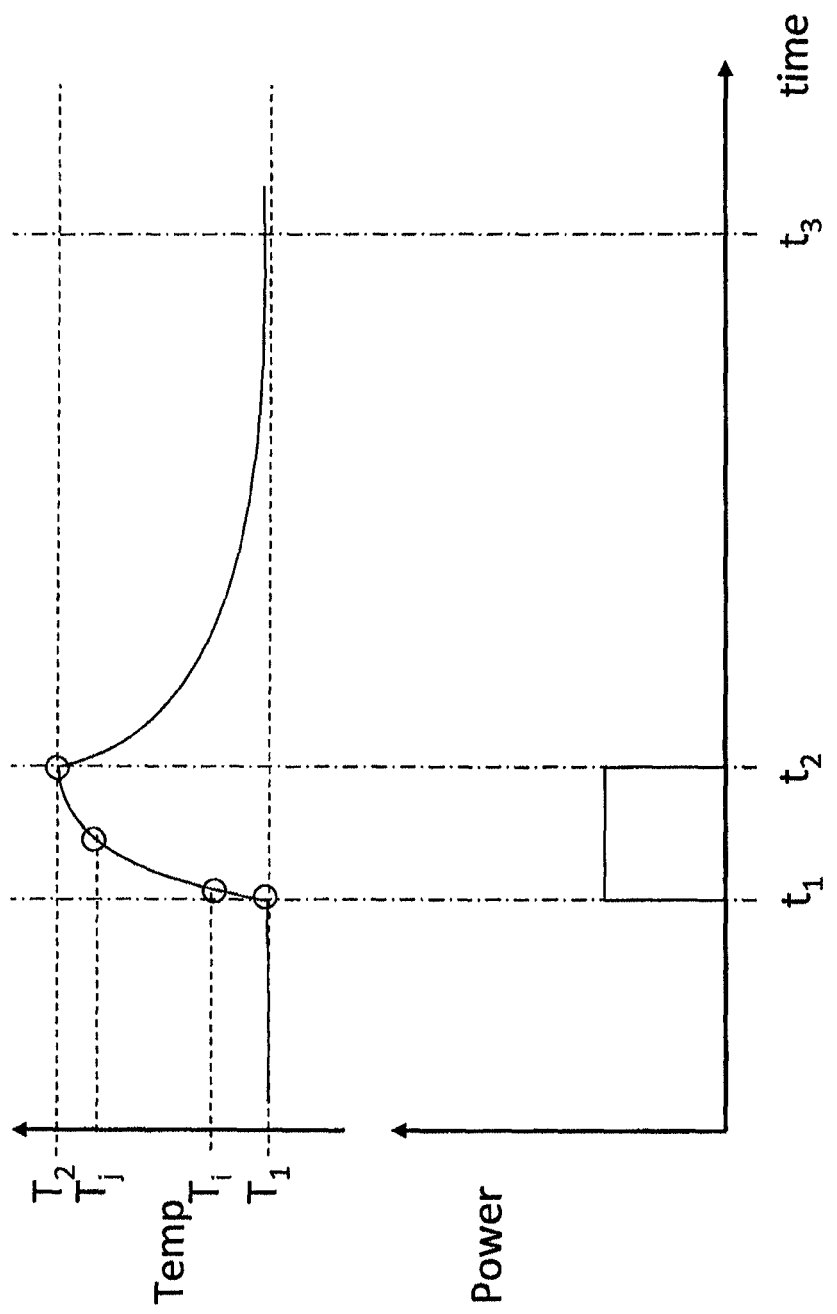

The heating pulse is not necessarily rectangular as illustrated in FIG. 3A and FIG. 3B. The pulse can be applied in various ways and have a variety of different waveforms such as a capacitor discharge pulse curve, as shown in FIG. 3C.

Figure 3C:
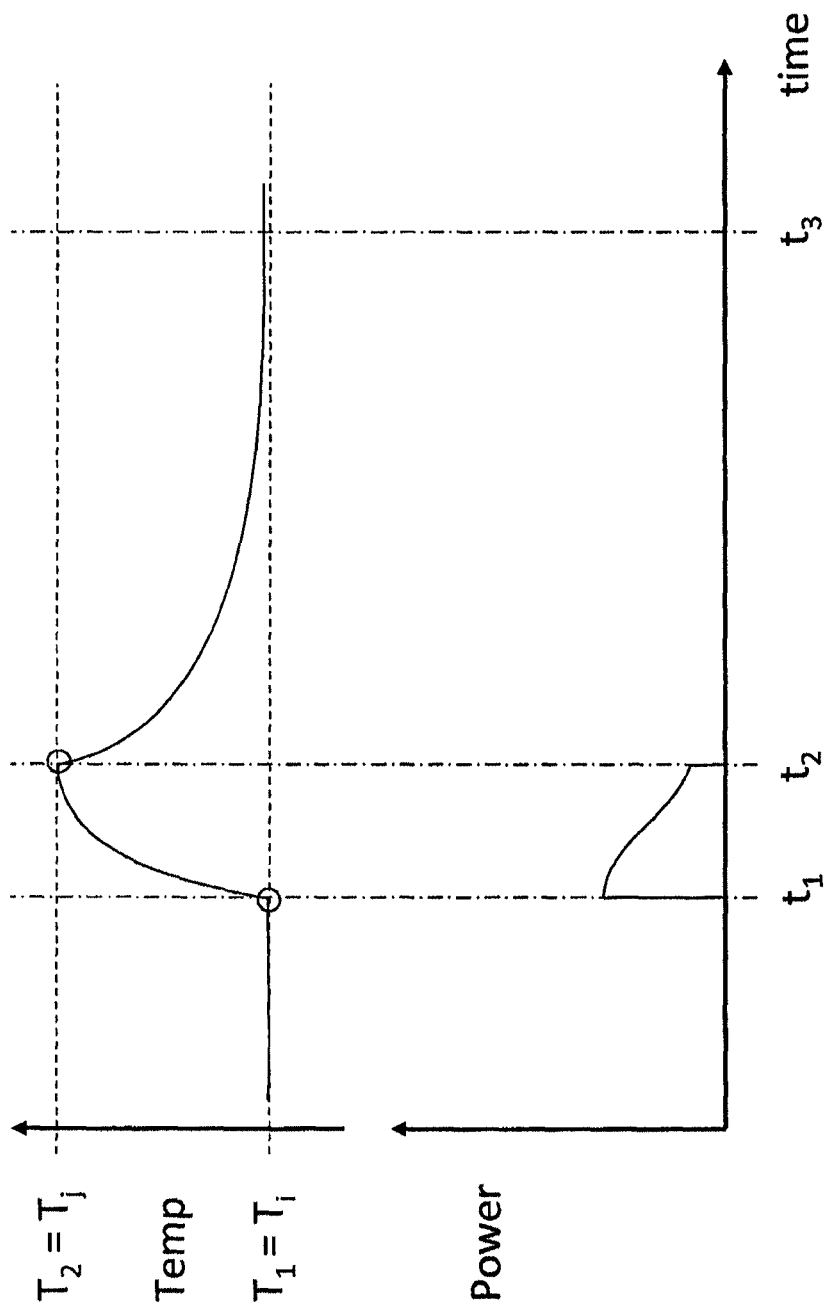

FIGS. 3A to 3C illustrate two important characteristics of the invention. Firstly, it can be seen from the temperature vs. time graphs that after the heating pulse has been applied, i.e. beginning at $t_2$, it may take a comparatively long time for the fluid flowing past the heating element to return its temperature to approximately its initial value at $t_3$. In the prior art it is necessary to wait until the temperature returns to within a narrow range of the original (ambient) temperature before another measurement can be made. Additionally, there are conditions where the ambient temperature is naturally changing. For example, for body fluids, the patient's body temperature naturally varies and the temperature of excreted biofluids, such as urine, will correspondingly vary. Similarly, the ambient temperature of the environment can vary and this may affect the temperature of the fluid. In such conditions, without an additional reference temperature sensor, it is impossible to know if the temperature read reflects the current ambient temperature of the liquid.

Figure 4:
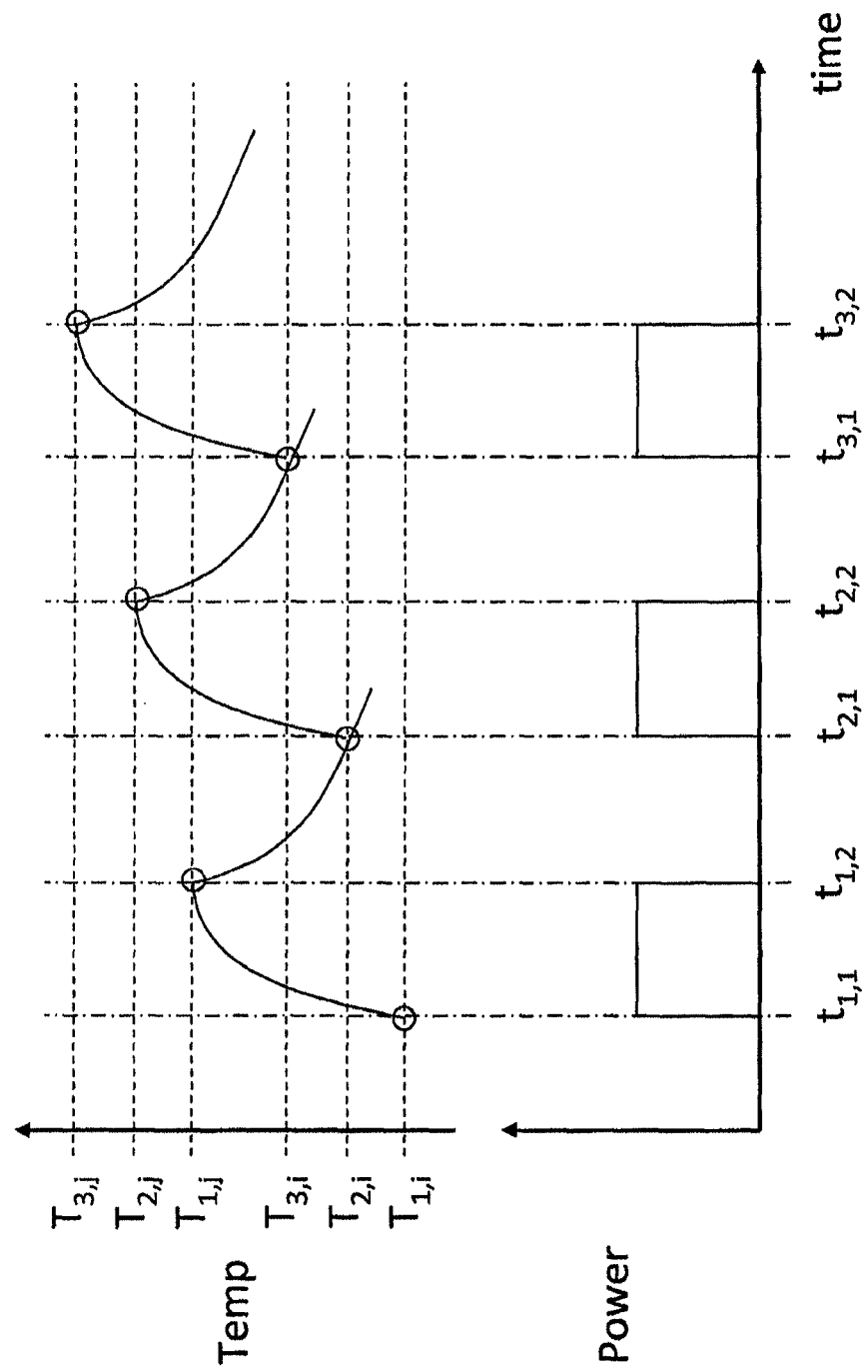
FIG. 4 schematically shows a series of three consecutive heating pulses and the corresponding temperature change vs. time.

In the present invention it is not necessary to wait until $t_3$ to apply the next heating pulse and begin another measurement cycle. Furthermore the starting temperature for the first measurement does not have to be the same as that of the second measurement. This is illustrated in FIG. 4, which shows a series of three consecutive heating pulses.

In order to use equation 6 to determine the flow rate, a series of measurements are made as above in which, for a given value of Q, the values of $\Delta T$ for various known flow rate values are carried out with the specific apparatus of the invention. This yields an empirically-derived table of data that maps flow rate to $\Delta T$ (or to a set of points representing a heat development curve). The calibration data is specific for the conduit, liquid in the conduit, components of the particular apparatus of the invention, and the value of Q. Because of the manner in which it is attained, the calibration data also takes into consideration the loss of heat to the conduit and the environment. The derived table can be used to determine a mathematical relationship in the form of an equation. Either the calibration table or graph (or a set of tables or graphs each for a different value of Q) are stored in a memory of the processor of the control system from which they can be retrieved from the memory to automatically determine the flow rate from the measured value of $\Delta T$.

The frequency of the measurements depends on the properties of the fluid flow being measured, e.g. if the flow rate is expected to be constant or rapidly varying, and on the significance of any changes in the flow rate, i.e. is it important to know as soon as possible of any change. In one embodiment the frequency is determined by the operator of the apparatus, for example, to be once every hour. According to another embodiment of the invention the frequency of measurements cycles is a function of the expected or actual rate of change of flow rate. Thus, for example, measurements can be made more frequently during the day when the change in flow rate is expected to be relatively high and less frequently at night when the change in flow rate is expected to be relatively low.

The timing of the measurements can also be determined automatically by the control system. In an embodiment after a heating pulse is applied the control system is programmed to detect when the temperature of the flowing liquid returns to its steady state value. When the control system detects the return to steady state it automatically reactivates the heating element in order to begin another cycle of measurements. In another embodiment the control system can determine the timing of a measurement based on the change in flow rate between a predetermined number of previous measurements The amount of energy that must be supplied to the heating element depends on the properties of the liquid and the flow rate. Appropriate values of energy in the pulse can be determined empirically for a given application. When flow rates are high, the heating dose that is applied may be increased to improve signal-to-noise ratio. In embodiments of the invention the processor of the control system may be adapted to automatically adjust the amount of energy applied according to the flow rate measured in the last heating pulse or according to the average flow rates or the extrapolation of a trend measured in a number of previous pulses, or when a prior measurement indicates insufficient heating (i.e., $\Delta T$ is below a specific value) or excess heating (i.e., $\Delta T$ is greater than a specific value).

Figure 5:
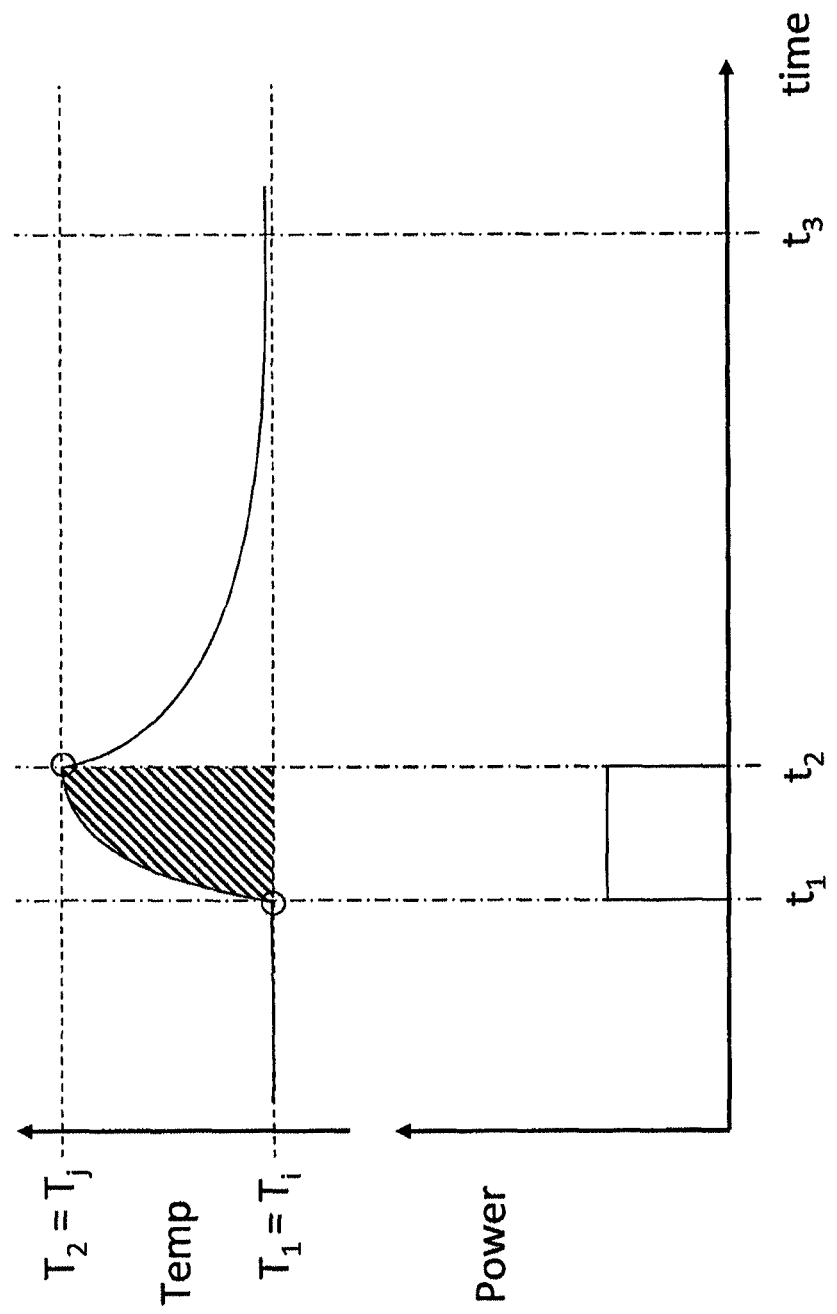
FIG. 5 schematically shows graphs of the power applied to the apparatus and the temperature change integral vs. time.

According to an embodiment of the invention illustrated in FIG. 5, the temperature is measured multiple times during the heating pulse, thereby obtaining a set of data points representing the temperature increase curve. The value of the integral of the resultant curve between $t_1$ and $t_2$ can be used as a measure of the flow rate. For a given value of Q in a pulse, the value of this integral is expected to decrease with increasing flow rate since as the flow rate increases more heat is lost and the temperature curve does not rise as it would at lower flow rates. Consequently, the area under the temperature curve between $t_1$ and $t_2$ is smaller. As in the other embodiments, calibration measurements can be made using known flow rates to construct look-up tables that relate the measured value of the integral to an unknown flow rate.

The sensor unit, i.e. the heating element and temperature sensor, of the apparatus of the invention can be provided as "built in" to dedicated flow lines or as separate units that can be attached to existing flow lines. For example to measure urine flow rate, the unit can have standard connections that allow it to be connected to the catheter on one side and a drainage tube, e.g., to a collection bag on the other side. In other embodiments it may be incorporated as an integral part of a catheter or of a drainage tube.

Figure 6:
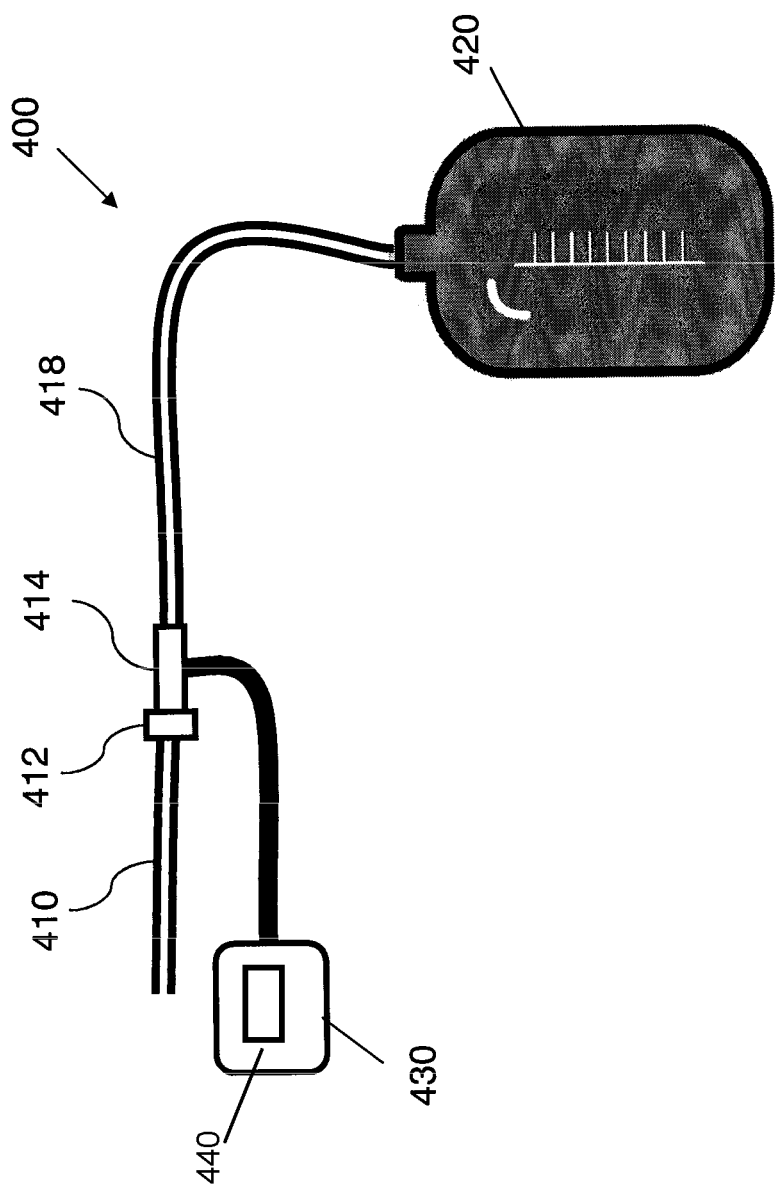
FIG. 6 schematically illustrates a system for measuring the flow rate of urine from a catheterized patient according to one embodiment of the invention.
Figure 7:
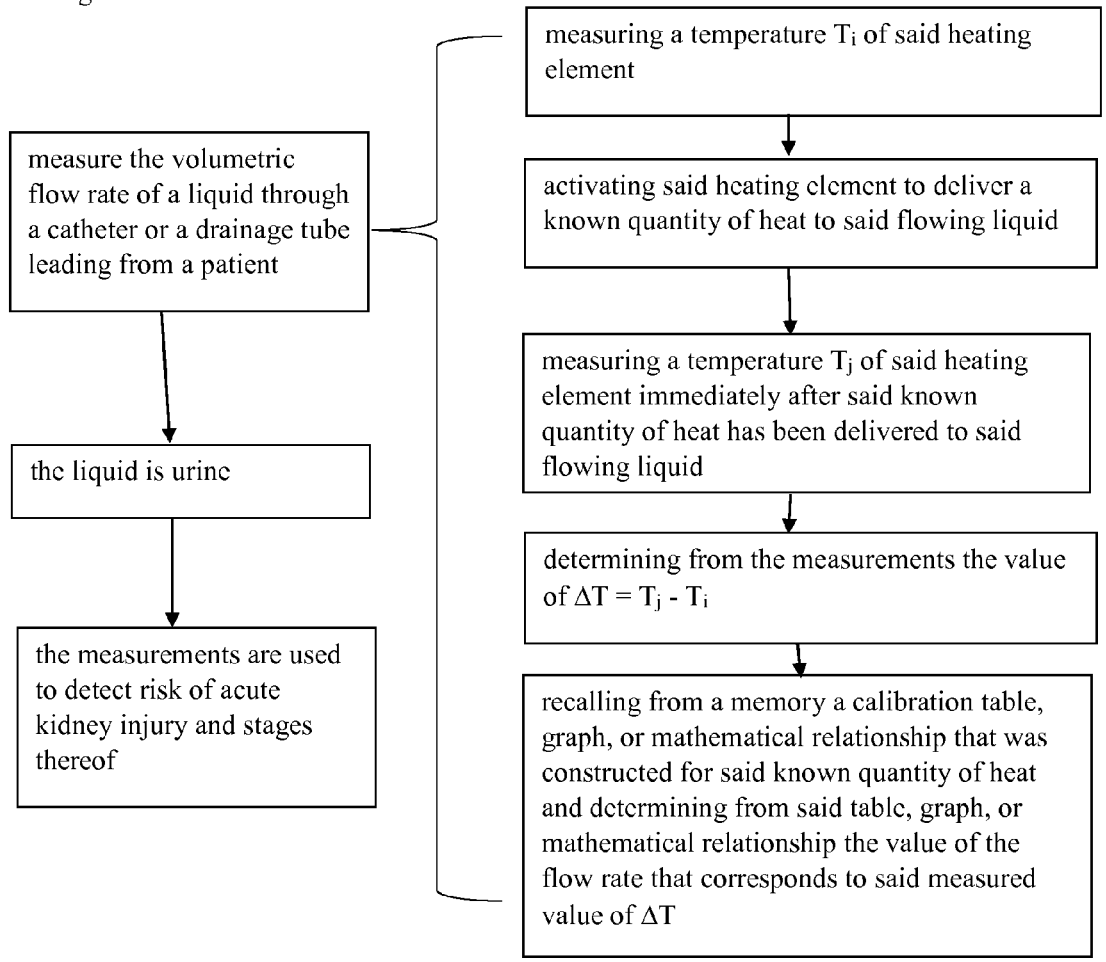
FIG. 7 illustrates a flow chart of a method for real-time measuring the volumetric rate of flow of a liquid through a conduit by use of an apparatus comprising a heating element in thermal contact with said flowing liquid and adapted to deliver a known quantity of heat to said flowing liquid, a temperature sensor adapted to measure the instantaneous temperature of said heating element, and a control system comprising a processor and a memory unit.
Figure 8:
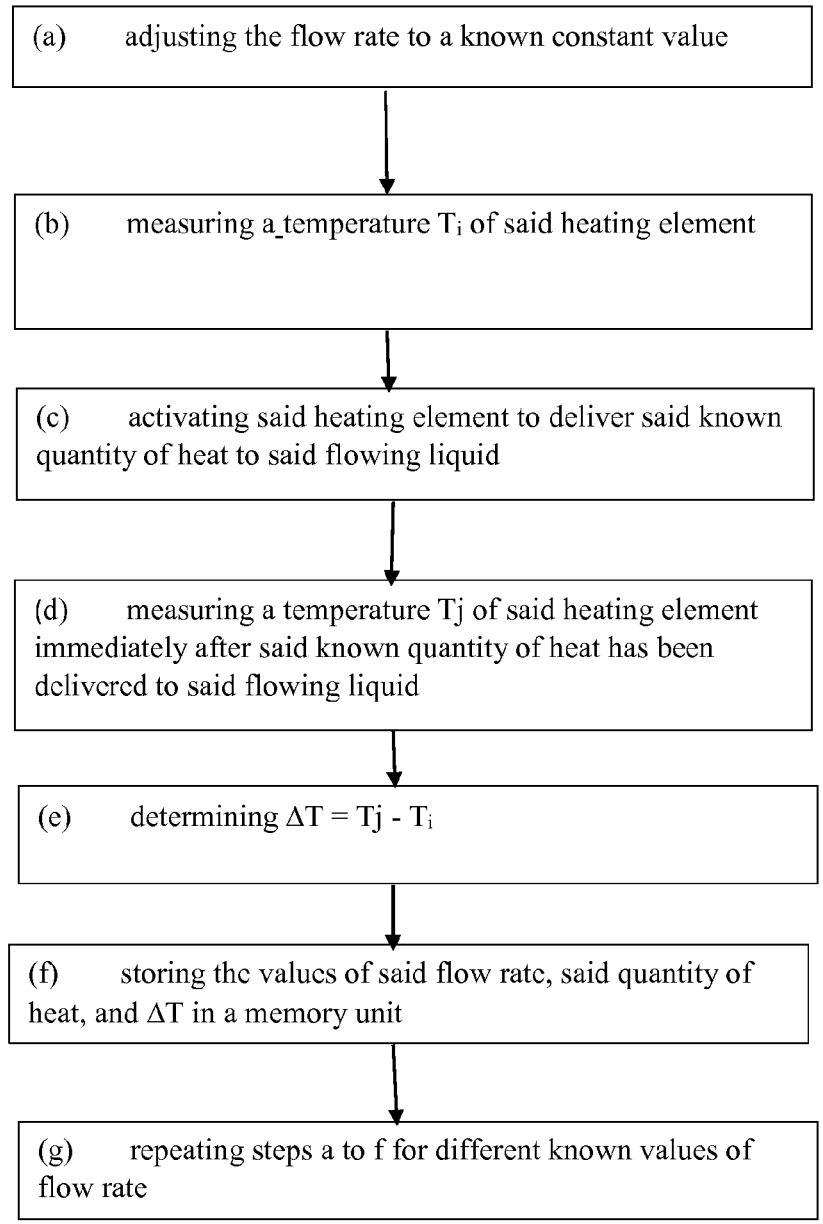
FIG. 8 illustrates a flow chart of a method of using a heating element in thermal contact with liquid flowing through a conduit and adapted to deliver a known quantity of heat to said flowing liquid and a temperature sensor adapted to measure the instantaneous temperature of said heating element to construct a calibration table, graph, or mathematical relationship that can be used to determine the value of the flow rate that corresponds to a measured value of $\Delta T$ for a known quantity of heat delivered by said heating element.
Figure 9:
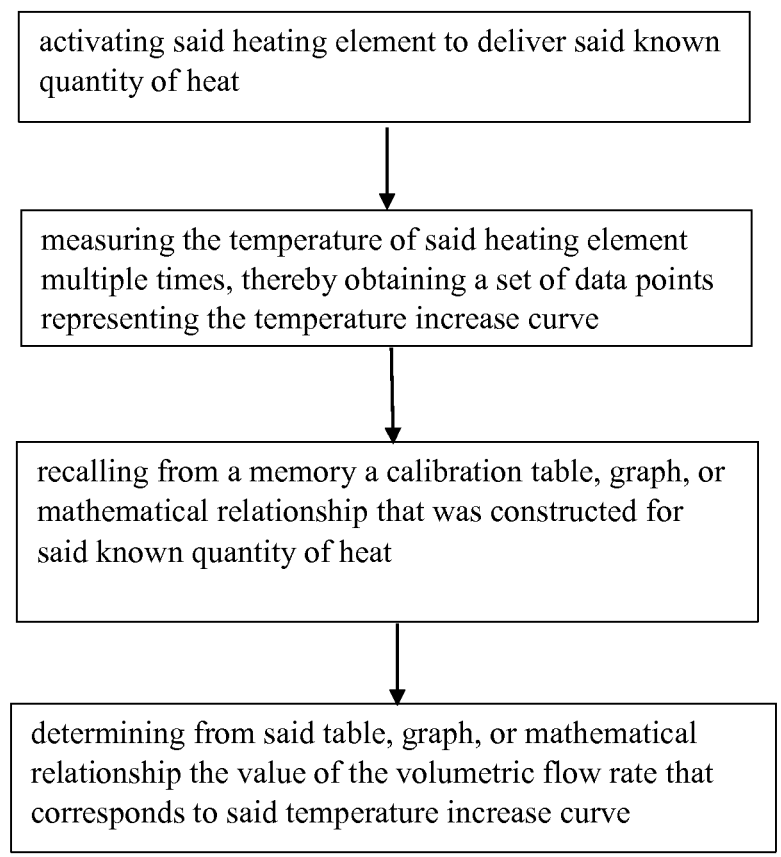
FIG. 9 illustrates a flow chart of a method for measuring the volumetric rate of flow of a liquid through a conduit by use of an apparatus comprising a heating element in thermal contact with said flowing liquid and adapted to deliver a known quantity of heat to said flowing liquid, a temperature sensor adapted to measure the instantaneous temperature of said heating element, and a control system comprising a processor and a memory unit.

FIG. 6 schematically illustrates an embodiment of a system 400 for measuring the flow rate of urine from a catheterized patient (not shown in the figure). Shown in the figure are catheter 410, sensor unit 414 (shown in detail in FIG. 2), drain tube 418, collection bag 420, and control system 430 comprising processor 440. An optional component of system 400 is bubble trap 412.

Although embodiments of the invention have been described by way of illustration, it will be understood that the invention may be carried out with many variations, modifications, and adaptations, without exceeding the scope of the claims.

The invention claimed is:

1. An apparatus for measuring the volumetric rate of flow of a liquid through a conduit, said apparatus comprising the following components:
   (a) a heating element in thermal contact with said liquid in said conduit, said heating element adapted to deliver a predetermined quantity of heat in a predetermined period of time to said flowing liquid;
   (b) a temperature sensor adapted to measure the instantaneous temperature of said heating element; and
   (c) a control system that comprises: a processor, input means, a memory unit, and output means, wherein:
      (i) said processor of said control system is configured to activate said heating element beginning at time $t_1$ and ending at $t_2$;
      (ii) said processor of said control system is configured to receive an initial measurement of the instantaneous temperature $T_i$ and a final measurement of the instantaneous temperature $T_j$ of said heating element from said temperature sensor, wherein $T_j$ is measured a predetermined period of time after the temperature $T_i$ is measured;
      (iii) said memory unit of said control system comprises pre-constructed calibration tables, graphs, or mathematical relationships that relate known values of flow rate to measured values of the change in temperature $T_j$-$T_i$ of said flowing liquid that take place during predetermined periods of time between measurements of $T_i$ and $T_j$ during which predetermined quantities of heat are delivered to said flowing liquid; and
      (iv) said apparatus is configured to measure the instantaneous value of $T_i$ after $t_1$ and said apparatus is configured to measure the instantaneous value of $T_j$ before $t_2$.

2. The apparatus of claim 1, further comprising a display device, wherein the components of said control system are configured to carry out at least one of the following:
   (a) said memory unit and display device of said control system are configured to store and display to a user information related to the operation of said apparatus and the properties of said liquid that are measured or determined by components of said apparatus;
   (b) said output means of said control system are configured to send instantaneous or historical values of measured temperatures and other information relative to said liquid and said apparatus to remote locations;
   (c) said output means of said control system are configured to send signals that can be used as input to other systems; and
   (d) said output means of said control system are configured to send alarms if there are predetermined changes in the flow rate or other measured properties of said liquid.

3. The apparatus of claim 1 comprising at least one of:
   (a) a bubble trap located upstream of a location at which the volumetric rate of flow is measured;
   (b) a gas-permeable membrane located upstream of said location at which the volumetric rate of flow is measured.

4. The apparatus of claim 1, wherein said apparatus is adapted to be either connected to or an integral part of a conduit.

5. The apparatus of claim 4, wherein said conduit is a catheter or drainage tube leading from a patient.

6. The apparatus of claim 5 wherein the processor of the control system is configured to use measurements of the flow rate of urine to provide on-going, real-time assessment of kidney function and early warning of conditions related to acute kidney injury (AKI).

7. A method for real-time measuring the volumetric rate of flow of a liquid through a conduit by use of an apparatus comprising a heating element in thermal contact with said flowing liquid and adapted to deliver a predetermined quantity of heat in a predetermined period of time to said flowing liquid, a temperature sensor adapted to measure the instantaneous temperature of said heating element, and a control system comprising a processor and a memory unit; said method comprising the following steps:
   (i) activating said heating element beginning at time $t_1$ and ending at time $t_2$;
   (ii) measuring a temperature $T_i$ of said heating element;
   (iii) measuring a temperature $T_j$ of said heating element a predetermined period of time after the temperature $T_i$ is measured; and
   (iv) recalling from said memory pre-constructed calibration tables, graphs, or mathematical relationships that relate known values of flow rate to measured values of the change in temperature $T_j$-$T_i$ of said flowing liquid that take place during predetermined periods of time between measurements of $T_i$ and $T_j$ during which predetermined quantities of heat are delivered to said flowing liquid;

wherein the instantaneous value of $T_i$ is measured after $t_1$ and the instantaneous value of $T_j$ is measured before $t_2$.

8. The method of claim 7, wherein said method is adapted to measure the volumetric flow rate of a liquid through a catheter or a drainage tube leading from a patient.

9. The method of claim 8, wherein the liquid is urine.

10. The method of claim 9, wherein the measurements are used to detect risk of acute kidney injury and stages thereof.

11. A method of using a heating element in thermal contact with liquid flowing through a conduit and adapted to deliver a predetermined quantity of heat in a predetermined period of time to said flowing liquid and a temperature sensor adapted to measure the instantaneous temperature of said heating element to construct a calibration table, graph, or mathematical relationship that can be used to determine a value of a flow rate, said method comprising the following steps:
 (a) adjusting a flow rate to a known constant value;
 (b) activating said heating element beginning at time t1 and ending at time t2;
 (c) measuring a temperature $T_i$ of said heating element;
 (d) measuring a temperature $T_j$ of said heating element a predetermined period of time after the temperature $T_i$ is measured;
 (e) storing the values of said flow rate, the value of the quantity of heat delivered to said flowing liquid in said predetermined period of time between measurements of $T_i$ and $T_j$, and the value of $T_j-T_i$ in a memory unit;
 (f) constructing a calibration table, graph, or mathematical relationship that relates said known value of flow rate to measured values of the change in temperature $T_j-T_i$ of said flowing liquid that take place during predetermined periods of time between measurements of $T_i$ and $T_j$ during which predetermined quantities of heat are delivered to said flowing liquid; and
 (g) repeating steps a to f for different known values of flow rate wherein the instantaneous value of $T_i$ is measured after $t_1$ and the instantaneous value of $T_j$ is measured before $t_2$.

12. A method for measuring a volumetric rate of flow of a liquid through a conduit by use of an apparatus comprising a heating element in thermal contact with said flowing liquid and adapted to deliver a predetermined quantity of heat in a predetermined period of time to said flowing liquid, a temperature sensor adapted to measure the instantaneous temperature of said heating element, and a control system comprising a processor and a memory unit; said method comprising the following steps:
 (a) activating said heating element beginning at time ti and ending at time t2 to deliver a predetermined quantity of heat;
 (b) measuring the temperature of said heating element multiple times, thereby obtaining a set of data points representing a temperature increase curve;
 (c) recalling from a memory graphs that relate known values of flow rate to measured values of the change in temperature $T_j-T_i$ of said flowing liquid that take place during predetermined periods of time between measurements of $T_i$ and $T_j$ during which predetermined quantities of heat are delivered to said flowing liquid; and
 (d) determining from said graphs a value of a volumetric rate of flow that corresponds to said temperature increase curve;
wherein the multiple measurements of instantaneous values of the temperature of said heating element are all measured after $t_1$ and before $t_2$.

* * * * *

UNITED STATES PATENT AND TRADEMARK OFFICE
CERTIFICATE OF CORRECTION

PATENT NO. : 9,857,210 B2  
APPLICATION NO. : 14/125348  
DATED : January 2, 2018  
INVENTOR(S) : Jack Yehoshua Mantinband et al.

Page 1 of 1

It is certified that error appears in the above-identified patent and that said Letters Patent is hereby corrected as shown below:

On the Title Page

Item (75), Adding an inventor:  
Mor GRINSTEIN  
Resident of  
Modi'in, Israel

Signed and Sealed this  
Sixth Day of November, 2018

Andrei Iancu  
*Director of the United States Patent and Trademark Office*